United States Patent [19]

Nitsche

[11] Patent Number: 5,240,909
[45] Date of Patent: Aug. 31, 1993

[54] USE OF LACTOFERRIN FOR TREATMENT OF TOXIC EFFECTS OF ENDOTOXINS

[76] Inventor: Dietrich Nitsche, Bismarckallee 2, 2300 Kiel, Fed. Rep. of Germany

[21] Appl. No.: 834,327
[22] PCT Filed: Mar. 13, 1991
[86] PCT No.: PCT/DE91/00214
  § 371 Date: Jan. 13, 1992
  § 102(e) Date: Jan. 13, 1992
[87] PCT Pub. No.: WO91/13629
  PCT Pub. Date: Sep. 19, 1991

[30] Foreign Application Priority Data

Mar. 14, 1990 [DE] Fed. Rep. of Germany ....... 4008033

[51] Int. Cl.$^5$ .................... A61K 37/02; A61K 37/14
[52] U.S. Cl. ............................................ 514/8; 514/6; 530/350; 530/380; 424/85.1; 424/85.8
[58] Field of Search ............... 514/8, 6; 424/85.1, 424/85.8; 530/350, 380

[56] References Cited

U.S. PATENT DOCUMENTS 4,726,948  2/1988  Prieels ................................ 424/94.4
4,780,529  10/1988  Hao ..................................... 530/380

FOREIGN PATENT DOCUMENTS 0385118  9/1990  European Pat. Off. .

OTHER PUBLICATIONS

Berger et al, Bacterial Endotoxins: Pathophysiological Effects, Clinical Significance & Pharm. Control, pp. 115–124.
Arnold et al, Inf. & Immun. vol. 32, No. 2, pp. 655–660, May 1981.
Arnold et al, Inf. & Immun. vol. 28, No. 3, pp. 893–898, Jun. 1980.
Sawatzki et al, Blood Cells (1989) vol. 15: 371–385.
Sawatzki et al, Biol. Abs. vol. 88 (1989) #58115.
Stacky et al, Chem Abs. vol. 109, #216033e, #13499d, #134994e, Mar. 1988.

Primary Examiner—Michael G. Wityshyn
Assistant Examiner—Choon Koh
Attorney, Agent, or Firm—Herbert W. Larson

[57] ABSTRACT

Animal species are treated either intravenously or by tube directly to the gut with a solution containing a lactoferrin bound to a metal ion, the metal ion content being at least 0.1 mg per gram of lactoferrin. The dose is sufficient to inhibit endotoxins.

17 Claims, 2 Drawing Sheets

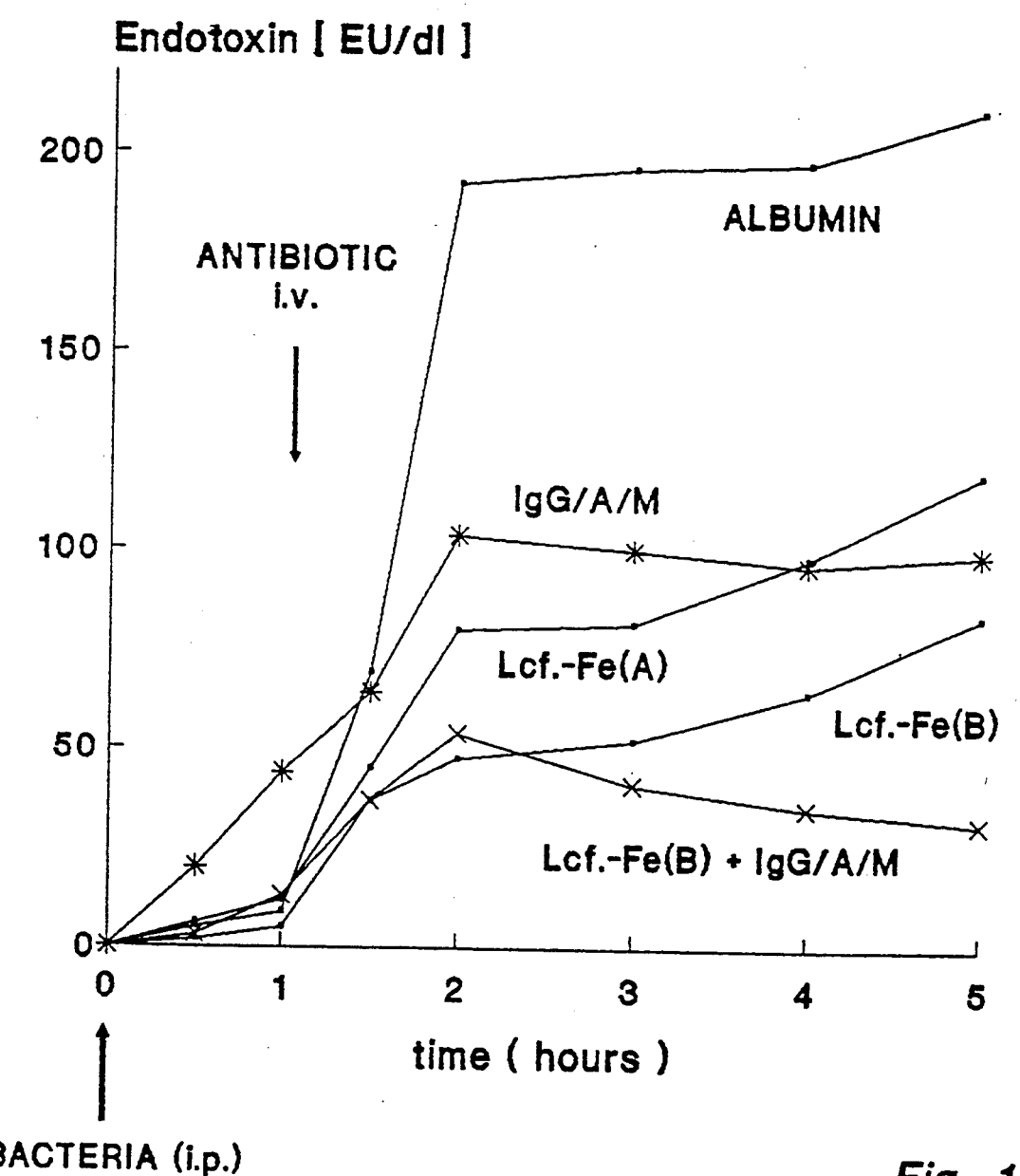
Fig.: 1

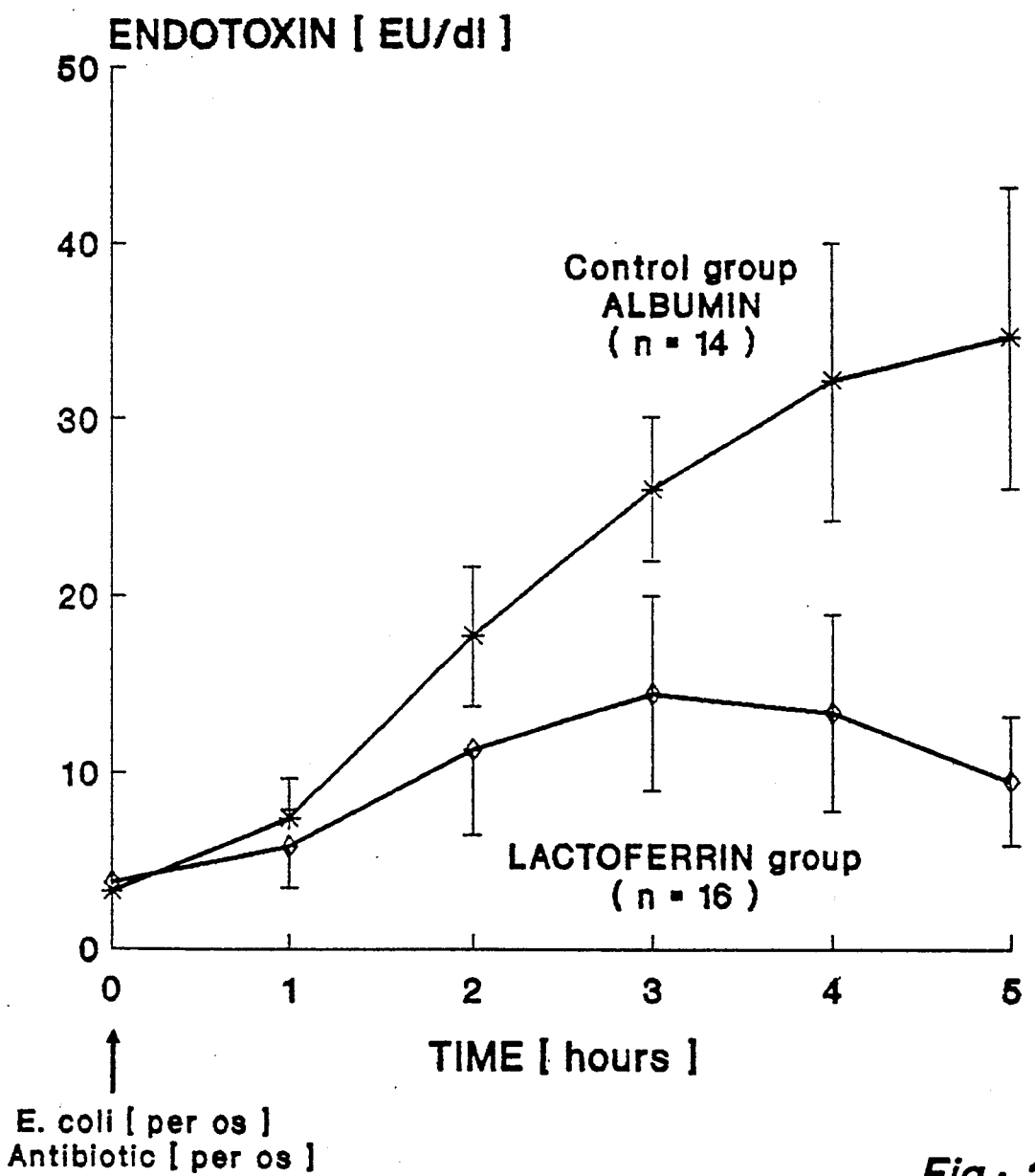

USE OF LACTOFERRIN FOR TREATMENT OF TOXIC EFFECTS OF ENDOTOXINS

BACKGROUND OF THE INVENTION

The invention relates to the use of lactoferrin as an agent for the propylactic and therapeutic treatment of the toxic effects of endotoxins.

Lactoferrin is a glycoprotein with an average molecular weight of 77,000 Dalton. It can bind two molecules of iron reversibly. It can also bind other bivalent or trivalent metal ions instead of iron such as copper, magnesium, zinc, manganese and cobalt.

Lactoferrin was first isolated from milk in 1960. The lactoferrin content of human milk is approx. 1 mg/dl. Lactoferrin has also been found in the blood, in the granula of the neutrophil granulocytes, in lacrimal fluid, in gastric fluid and in the secretions of the intestinal tract. The lactoferrin concentration found in the blood ranges from 40 to 200 µg/dl.

Lactoferrin in the blood, which is released mainly by the granula of the neutrophil granulocytes, contributes to some aspects of iron transport to the cells of the reticulo-endothelial system, especially during infections or inflammatory processes. [Van Snick JL, Masson L, Heremans JF. The involvement of lactoferrin in the hyposideremia of acute inflamation. J Exp Med 1974; 140: 1068-1084]. In animal experiments, due to the rapid release of lactoferrin from the granulocytes, the administration of endotoxin or bacteria was seen to be nearly concurrent with the increase in plasma lactoferrin levels. For this reason, an increase in plasma lactoferrin concentration is considered to be an early indicator for endotoxemia or septicemia (Gutteberg TJ., Rokke O., Joergensen T.; Andersen O.,: Lactoferrin as an Indicator of septicemia and Endotoxemia in Pigs. Scand J Infect Dis (1988), 20: 659-666).

Another essential function of lactoferrin, particularly in the neonatal period, is the regulation of iron absorption in the intestinal tract [Brock JH, Lactoferrin in human milk: its role in iron absorption and protection against enteric infections in the newborn infant. Arch Dis Child (1980) 55: 417-422], since the lactoferrin in human milk is capable of releasing the bound iron to the cells of the gut mucosa.

The most important biological function of lactoferrin derives, however, from its bacteriostatic effect [Arnold RR, Brewer M, Gauthier JJ. Bactericidal activity of human Lactoferrin: Sensitivity of a variety of microorganisms. Infection and Immunity (1980) 28: 893-898; Arnold RR, Russel JE, Champion WJ, Gauthier JJ. Bactericidal activity of human Lactoferrin: influence of physical conditions and metabolic state of the target microorganisms. Infection and Immunity (1981) 32: 655-660; Gutteberg T.J., Rokke O., Andersen O., Joergensen T.; Early Fall of Circulating Iron and Rapid Rise of Lactoferrin in Septicemia and Endotoxemia: An Early Defence Mechanism. Scand J Infect Dis;(1989) 21: 709-715]. Due to its bacteriostatic effect, the lactoferrin in human milk plays an important role as a defense mechanism in that it protects the newborn against intestinal infections. This bacteriostatic effect results from the high iron-binding capacity of lactoferrin. Iron is an essential growth factor for bacteria. The complexing of iron and lactoferrin keeps the concentration of free iron around the bacteria below the level conducive to bacterial growth. This results in an inhibition of bacterial growth. The higher the iron content, the less bacteriostatic effect lactoferrin has. Since iron-free lactoferrin (apoform) is released as early as the initial phase of bacteriemia and endotoxemia, GUTTEBERG et al. assumed that iron-free lactoferrin, in view of its bacteriostatic effect, might be an early defense mechanism against bacterial invasion [Gutteberg T.J., Rokke O., Andersen O., Joergensen T.; Early Fall of Circulating Iron and Rapid Rise of Lactoferrin in Septicemia and Endotoxemia: An Early Defence Mechanism. Scand. J. Infect. Dis.,(1989), 21: 709-715]. The publication cited above does not contain any evidence that the iron-free apoform of lactoferrin released from granulocytes plays the role of a defense mechanism against the endotoxin in addition to its function as a defense mechanism against bacteria.

Lactoferrin also seems to fulfil some function in the physiological regulation of granulopoiesis, whereby the mechanism involved is not yet fully understood. It has been observed that the release of the colony stimulating factor (CSF) from the macrophages can be inhibited by lactoferrin. This factor is essential for granulopoiesis. The inhibition of CSF release depends on the iron load of the lactorferrin [Broxmeyer HE et al. Identification of lactoferrin as the granulocyte-derived inhibitor of colony-stimulating activity production. J Exp Med 1978; 148: 1052-1068].

Endotoxin is a constituent of the cellular walls of gram-negative bacteria and is released only by the bacterial decay. It is a macromolecule with a molecular weight of up to $1 \times 10^6$ Dalton, consisting mainly of sugar compounds and fatty acids. It may also include complexed protein residues from the wall of the bacteria. The endotoxin molecule consists of three structurally and immunobiologically different subregions:

Subregion 1, the O-specific chain, consists of several repetitive oligosaccharide units, each of which is made up of a maximum of 5 neutral sugars. The number of oligosaccharides present depends on the strain of bacteria; for example, the endotoxin of S. abortus equi used in our experiments has 8 oligosaccharides in this region.

Subregion 2, the core oligosaccharide, consists, among other things, of n-acetyl-glucosamine, glucose, galactose, heptose and 2-keto-3-desoxyoctone acid.

Subregion 3, The lipid A (MW 2,000 Dalton) consists of a phosphorylated D-glucosamine-disaccharide to which several - approx. 7 - long-chain fatty acids are bound as amides and esters. The carrier of the toxic properties is the lipid A, whereby the toxic effects derive from several fatty acid residues in this region.

The size of the endotoxin molecule and its charge characteristics allow for complexing various compounds and proteins with the groups or side-chains of the three subregions in the endotoxin structure without this having any influence on its toxic properties. Normally, there is a protein bound to the lipid A, the so-called lipid A-associated protein. In most cases, separation of this protein component from the endotoxin causes no change whatever in the toxic effect. It was, however, found that binding of proteins onto many endotoxins can also result in a considerable increase in their toxicity (Rietschel E.TH. et al. (1982)): "Bacterial Endotoxins: Chemical Structure, Biological Activity and Role in Septicaemia", Scand. J. Infect. Dis. Suppl. 31: 8-21; p. 17).

There is also a physiological transfer of endotoxin from the intestine into the blood in healthy persons. Elimination of endotoxin from portal vein blood seems to occur mainly in the liver. To protect organs from damage, plasma in healthy persons can inactivate the endotoxin that is continually transferred from the intestine, although the mechanism has not yet been explained. Intestinal permeability disturbances may result in increased transfer of endotoxin from the intestine into the bloodstream. Such disturbances occur, for example, following disturbances of microcirculation due to shock or inflammatory intestinal diseases or under immunosuppressive therapy with Ciclosporin A. Increased endotoxin transfer from the intestine into the blood is also observed following enteral antibiotic therapy leading to increased endotoxin release in the intestine (NITSCHE D, STEHLE M, HAMELMANN H, Der Einfluß der Immunsuppression mit Ciclosporin auf die enterogene Endotoxinämie: Tierexperimentelle Untersuchungen. Langenbecks Archiv für Chirurgie, 1990, Suppl.). Release of large amounts of endotoxins, and therefore increased transfer of endotoxin from the septic focus into the bloodstream may also occur in cases of extensive gram-negative infection such as peritonitis. Such a massive influx of endotoxins exhausts the plasma's capacity to inactivate these endotoxins quickly enough, leading to higher plasma levels of biologically active endotoxin and resulting, finally in clinical endotoxemia. On the one hand, endotoxin causes the release of toxic mediators; on the other hand, it also disturbs the energy metabolism of the cell, resulting in cell decay and—in the case of a higher dose of endotoxin and/or a longer duration of the endotoxemia - organ failure as well. For this reason, all diseases involving the possibility of increased endotoxin transfer from the intestine or from a septic focus into the blood, or which involve a disturbance of the physiological elimination of endotoxin by the liver, require additional therapeutic measures capable of reducing endotoxin activity in the blood.

An important additional therapeutic measure in treatment of endotoxemia is the reduction of the influx of endotoxins from the intestine, which is also continuous under physiological conditions.

Oral administration of substances capable of adsorbing endotoxin has been proposed as a therapeutic measure to reduce the influx of endotoxin from the intestine into the blood [Ditter B, Urbaschek R, Urbaschek B. Ability of various adsorbents to bind endotoxins in vitro and to prevent orally induced endotoxemia in mice. Gastro-enterology 1983; 84:1547–1552]. The main problem involved in using these substances is that they succeed in binding the endotoxins in the intestine, but do not inactivate their toxic properties, so that toxic endotoxins might be released once again as a result of a chemical change in the ambient milieu.

As demonstrated by clinical trials, it is possible to reduce plasma endotoxin activity by administering monoclonal lipid A antibodies [Ziegler EJ et al; Treatment of gram-negative bacteremia and septic shock with HA-1A human monoclonal antibody against endotoxin. N Eng J Med, 1991:429–436]. Plasma endotoxin activity can also be reduced to a certain degree by administering polyvalent immunoglobulin preparations, since they can be expected to contain a certain amount of lipid A antibodies. With the exception of the preparations containing monoclonal lipid A antibodies, however, all of the therapeutic means available to date are marred by the disadvantage that they inactivate only a certain percentage of the endotoxins entering the blood. For this reason, they prove ineffective when larger amounts of endotoxins enter the bloodstream.

SUMMARY OF THE INVENTION

It is the object of this invention to provide a therapeutic agent suitable as a means of controlling the toxic effects of endotoxin by virtue of its ability to neutralize large amounts of plasma endotoxin rapidly. It should also be capable of reducing the physiological influx from the intestinal tract into the bloodstream by inactivating the endotoxins released in the intestine while they are still inside the intestinal tract. It must be possible for this purpose to administer the agent orally or through a gastric tube.

The invention thus provides for the use of lactoferrin that has bound a metal ion. Such lactoferrin can be administered either parenterally or enterally. The lactoferrin used must have bound either iron or another metal ion. A combination of lactoferrin with immunoglobins containing either only IgG or a combination of all three: IgG, IgM and IgA, has proven very effective. It is also possible to enrich lactoferrin for parenteral application in plasma derivatives in order to combine it with the proteins found in them. Lactoferrin used for parenteral applications must be equivalent to human lactoferrin. Lactoferrin from animal sources can be used in enteral applications.

BRIEF DESCRIPTION OF THE DRAWINGS

FIG. 1 is a graph showing the influence of intravenous applied lactoferrin and intravenous immunoglobulin on endotoxin activity in animals.

FIG. 2 is a graph showing the treatment of gut derived endotoxemia by enteral administration of lactoferrin in animals.

DETAILED DESCRIPTION OF THE INVENTION

The following experiments were carried out to test endotoxin inactivation by lactoferrin alone as well as by a combination of lactoferrin with immunoglobins: The influence of metal ions was tested using iron and zinc. Human and bovine lactoferrin in iron-free apoform and lactoferrin that had bound iron or zinc were tested alone, as well as in combination with immunoglobin preparations, in vitro and in vivo, to determine their capacity for reducing the biological activity of endotoxins.

In vitro experiments:

A) Quantitative investigations of influence on biological activity:

Human lactoferrin and bovine lactoferrin combined with immunoglobulins were incubated with increasing amounts of endotoxin at 37° C. for 60 minutes. Following incubation, quantitative determination of the biological activity of endotoxin in the supernatant was carried out with a modification of the Limulus test using a chromogenic substrate (Nitsche et al. In: Watson SW, Levin J, Novitsky TJ (eds.) DETECTION OF BACTERIAL ENDOTOXINS WITH THE LIMULUS AMEBOCYTE LYSATE TEST, pp. 417–429 (1987)). The lower detection limit in this modified version of the Limulus test is 1 EU/dl [1 EU/dl=100 pg/dl EC-5]. The endotoxin activity measured by the Limulus test corresponds to the biological activity of the endotoxin (Nitsche D, Flad HD and Blum B, Endotoxin determination by the Limulus test and the biological activity of endotoxin. Does a correlation exist? - in preparation).

The human and bovine lactoferrin used in the experiments was almost iron-free (Lcf.−0). The iron assay method described by Megraw and Bouda (Megraw RE, Hritz AM, Babson AL and Carroll JJ (1973) Clin. Biochem. 6: 266; Bouda J (1968) Clin. Chem. Acta 21:159) revealed no iron content in the 5% solution of apolactoferrin (Lcf.−0) down to the lowest detection limit (0.3 μg/dl). No zinc was detected in this apolactoferrin (Lcf.−0) by means of atomic absorption spectroscopy.

Following dissolution in normal saline, the apolactoferrin was first sterilized by filtering it. Then varying amounts of iron chloride ($FeCl_3$) were added to it to obtain lactoferrin solutions with varying iron contents.

In the experiments, lactoferrin (Lcf.−Fe(A)) was used the solution of which had an iron content of 28 μg of iron per gram of lactoferrin, lactoferrin (Lcf.−Fe(B)) with an iron content of 296 μg of iron per gram of lactoferrin and lactoferrin (Lcf.−Fe(C)) with an iron content of 1058 μg of iron per gram of lactoferrin.

Further sample preparations of apolactoferrin were made by adding zinc $ZnCl_2$ to apolactoferrin (Lcf.−0) to obtain an apolactoferrin solution (Lcf.−Zn) with a zinc content of 590 μg/g of apolactoferrin.

The following immunoglobulin preparations were used: 7S IgG (Intraglobin ®, Sandoglobin ®) as well as 7S IgG, enriched with 12% IgM (IgG/A/M=Pentaglobin ®).

Endotoxins from the following bacterial strains were used: Salmonella abortus equi (NOVOPYREXAL ®), Pseudomonas aeruginosa Fisher Type 7, as well as the FDA endotoxin standard von E.coli 0113:H10:K0.

DETERMINATION OF THE "MEAN PERCENTAGE OF INACTIVATION"

The percentage of the amount of endotoxin that was inactivated in each case was calculated from the difference between the initial endotoxin concentration and the endotoxin activity measured following incubation with the protein. The "mean percentage of inactivation" for each protein concentration for the entire range of endotoxin concentrations tested (10 EU/dl - 1000 EU/dl) was calculated on the basis of the values determined in this way for the different endotoxin concentrations.

DETERMINATION OF ENDOTOXIN INACTIVATION CAPACITY:

In order to quantify the capacity of lactoferrin and the combination of lactoferrin with immunoglobulins for inactivating endotoxin, the "INACTIVATION CAPACITY" was determined. To improve measurement precision, this parameter was not determined at equivalence, but rather at endotoxin excess concentrations of 10 EU/dl and 100 EU/dl.

This parameter was calculation on the basis of the amount of endotoxin (EU/dl) that had to be added to each protein preparation to reach a concentration of free endotoxins of 10 or 100 EU/dl in the supernatant following incubation (60 minutes, 37° C.) with the protein preparation. This endotoxin concentration was calculated for each preparation (lactoferrin, immunoglobin and the combination of lactoferrin and immunoglobin) on the basis of the relation between the amount of endotoxin added and the endotoxin concentration measured in the supernatant following incubation. This relation was determined by a series of measurements in which endotoxin in increasing concentrations (10 EU/dl, 25 EU/dl, 50 EU/dl, 100 EU/dl, 200 EU/dl, 300 EU/dl, 500 EU/dl, 750 EU/dl and 1,000 EU/dl) was incubated for 60 minutes together with the various protein preparations. The concentration of lactoferrin in the reaction preparation was 312.5 mg/dl.

Measurements carried out with the combination of lactoferrin and immunoglobulin revealed a concentration of each protein component of 312 mg/dl. The mean endotoxin concentration that can be inactivated by each protein preparation [mg/dl] under the given conditions is the amount of endotoxin determined in this way minus the given amount of excess endotoxin (10 EU/dl or 100 EU/dl). In relation to a protein concentration of 100 mg/dl, this amount of endotoxin is a gauge of the "mean inactivation capacity (EU/100 mg)" of each lactoferrin preparation or of the combination of lactoferrin with immunoglobulin.

RESULTS:

1. Lactoferrin:

When endotoxin is incubated with iron-free apolactoferrin (Lcf.−0), an average reduction in endotoxin activity of 35.4 to 41.2% is registered, depending on the type and concentration of endotoxin.

When endotoxin is incubated with lactoferrin (Lcf.−Fe(A)) with an iron content of 28 μg/g of lactoferrin, an average reduction in endotoxin activity of 62 to 67.7% is registered, depending on the type of endotoxin.

When endotoxin is incubated with lactoferrin (Lcf.−Fe(B)) with an iron content of 296 μg/g of lactoferrin, an average reduction in endotoxin activity of 79.1 to 86.4% is registered, depending on the type of endotoxin.

When endotoxin is incubated with lactoferrin (Lcf.−Fe(C)) with an iron content of 1,058 μg/g of lactoferrin, an average reduction in endotoxin activity of 89.2 to 96.7% is registered, depending on the type of endotoxin.

When endotoxin is incubated with apolactoferrin (Lcf.−Zn) with an zinc content of 590 μg/g of lactoferrin, an average reduction in endotoxin activity of 85.2 to 92.7% is registered, depending on the type of endotoxin.

a) On the basis of an endotoxin excess of 10 EU/dl, the inactivation capacity is:

I.) Lcf.−0: For S.abortus equi 5.8 EU/100 mg, for E.coli 5.2 EU/100 mg and for Pseudomonas aeruginosa 4.7 EU/100 mg.

II.) Lcf.−Fe(A): For S.abortus equi 48.9 EU/100 mg, for E.coli 57.8 EU/100 mg and for Pseudomonas aeruginosa 17.5 EU/100 mg.

III.) Lcf.−Fe(B): For S.abortus equi 62.1 EU/100 mg, for E. coli 72.3 EU/100 mg and for Pseudomonas aeruginosa 67.7 EU/100 mg.

IV.) Lcf.−Fe(C): For S.abortus equi 97.1 EU/100 mg, for E. coli 126.4 EU/100 mg and for Pseudomonas aeruginosa 152.7 EU/100 mg.

V.) Lcf.−Zn: For S.abortus equi 85.6 EU/100 mg, for E. coli 109.6 EU/100 mg and for Pseudomonas aeruginosa 126.8 EU/100 mg.

b) On the basis of an endotoxin excess of 100 EU/dl, the inactivation capacity is:

I.) Lcf.−0: For S.abortus equi 20.3 EU/100 mg, for E coli 18.8 EU/100 mg and for Pseudomonas aeruginosa 32.7 EU/100 mg.

II.) Lcf.−Fe(A): For S.abortus equi 167.9 EU/100 mg, for E.coli 309 EU/100 mg and for Pseudomonas aeruginosa 155.4 EU/100 mg.

III.) Lcf.−Fe(B): For S.abortus equi 233 EU/100 mg, for E.coli 493.2 EU/100 mg and for Pseudomonas aeruginosa 392.4 EU/100 mg.

IV.) Lcf.—Fe(C): For *S.abortus* equi 376.5 EU/100 mg, for *E. coli* 598 EU/100 mg and for *Pseudomonas aeruginosa* 627 EU/100 mg.

V.) Lcf.—Zn: For *S.abortus* equi 312.6 EU/100 mg, for *E. coli* 527 EU/100 mg and for *Pseudomonas aeruginosa* 558.8 EU/100 mg.

2. Lactoferrin and 7S IgG:

The combination of lactoferrin with a 7S IgG preparation improves inactivation of endotoxin. Incubation of endotoxin with 7S IgG alone (312 mg/dl) reduces endotoxin activity by 21.5 to 33.7%. When endotoxin is incubated with a combination of lactoferrin (312 mg/dl) and 7S IgG (312 mg/dl) for an endotoxin concentration range below 200 EU/dl when iron-free apolactoferrin (Lcf.—0) is used, endotoxin activity is reduced by 58.7 to 64.1%. For higher endotoxin concentrations this combination reduces endotoxin activity by only 44.3 to 51.8%. When lactoferrin (Lcf.—Fe(A)) with an iron content of 28 μg of $Fe^{3+}$ per gram of lactoferrin is used instead, a reduction in endotoxin activity of 72 to 78.4% is registered, depending on the type and concentration of the endotoxin used.

When lactoferrin (Lcf.—Fe(B)) with an iron content of 950 μg per gram of lactoferrin is used in combination with 7S IgG, endotoxin activity is reduced by 87.3 to 92.2%, depending on the type and concentration of the endotoxin.

a) On the basis of an endotoxin excess of 10 EU/dl, the inactivation capacity is:

I.) Sole use of 7S IgG: For *S.abortus* equi 1.8 EU/100 mg, for *E. coli* 0.9 EU/100 mg and for *Pseudomonas aeruginosa* 1.3 EU/100 mg.

II ) Lcf.—0 and 7S IgG: For *S.abortus* equi 9.1 EU/100 mg, for *E.coli* 12.6 EU/100 mg and for *Pseudomonas aeruginosa* 10.4 EU/100 mg.

III.) Lcf.—Fe(A) and 7S IgG: For *S.abortus* equi 57.6 EU/100 mg, for *E. coli* 65.7 EU/100 mg and for *Pseudomonas aeruginosa* 36.2 EU/100 mg.

IV.) Lcf.—Fe(B) and 7S IgG: For *S. abortus* equi 77.4 EU/100 mg, for *E. coli* 86.4 EU/100 mg and for *Pseudomonas aeruginosa* 82.7 EU/100 mg.

b) On the basis of an endotoxin excess of 100 EU/dl, the inactivation capacity is:

I.) Sole use of 7S IgG: For *S. abortus* equi 19.3 EU/100 mg, for *E. coli* 9.4 EU/100 mg and for *Pseudomonas aeruginosa* 16.7 EU/100 mg.

II.) Lcf.—0 and 7S IgG: For *S. abortus* equi 47.6 EU/100 mg, for *E. coli* 51.9 EU/100 mg and for *Pseudomonas aeruginosa* 57.3 EU/100 mg.

III.) Lcf.—Fe(A) and 7S IgG: For *S. abortus* equi 202 EU/100 mg, for *E. coli* 359 EU/100 mg and for *Pseudomonas aeruginosa* 282.5 EU/100 mg.

IV.) Lcf.—Fe(B) and 7S IgG: For *S. abortus* equi 289.7 EU/100 mg, for *E. coli* 545.2 EU/100 mg and for *Pseudomonas aeruginosa* 447.1 EU/100 mg.

3. Lactoferrin and IgG/A/M (12% IgM):

The addition of lactoferrin to an IgG preparation enriched with 12% IgM (IgG/A/M) causes a further improvement in inactivation capacity. Endotoxin activity is reduced by approx. 45 to 48% by IgG/A/M (12% IgM) (312 mg/dl) used alone. When endotoxin is incubated with the combination of IgG/A/M (12% IgM) (312 mg/dl) and lactoferrin (also 312 mg/dl), endotoxin activity is reduced by 75.9 to 81.2%, depending on the type of endotoxin, when lactoferrin (Lcf.—Fe(A)) with an iron content of 28 μg per gram of lactoferrin is used.

When lactoferrin (Lcf.—Fe(B)) containing 296 μg of iron per gram of lactoferrin and IgG/A/M are combined, endotoxin activity is reduced by 91.8 to 95.4%, depending on the type and concentration of endotoxin.

a) On the basis of an endotoxin excess of 10 EU/dl, the inactivation capacity is:

I.) Sole use of IgG/A/M(12% IgM): For *S.abortus* equi 5.1 EU/100 mg, for *E.coli* 3.8 EU/100 mg and for *Pseudomonas aeruginosa* 5.7 EU/100 mg.

II.) Lcf.—Fe(A) and IgG/A/M: For *S.abortus* equi 68.6 EU/100 mg, for *E. coli* 74.4 EU/100 mg and for *Pseudomonas aeruginosa* 51.2 EU/100 mg.

III.) Lcf.—Fe(B) and IgG/A/M: For *S. abortus* equi 87.4 EU/100 mg, for *E. coli* 97.8 EU/100 mg and for *Pseudomonas aeruginosa* 96.7 EU/100 mg.

b) On the basis of an endotoxin excess of 100 EU/dl, the inactivation capacity is:

I.) Sole use of IgG/A/M(12% IgM): For *S.abortus* equi 48.9 EU/100 mg, for *E. coli* 35.7 EU/100 mg and for *Pseudomonas aeruginosa* 67.7 EU/100 mg.

II.) Lcf.—Fe(A) and IgG/A/M: For *S. abortus* equi 268.4 EU/100 mg, for *E. coli* 419.1 EU/100 mg and for *Pseudomonas aeruginosa* 394.5 EU/100 mg.

III.) Lcf.—Fe(B) and IgG/A/M: For *S.abortus* equi 383.7 EU/100 mg, for *E. coli* 629.4 EU/100 mg and for *Pseudomonas aeruginosa* 586.7 EU/100 mg.

B) INFLUENCE ON RELEASE OF THE MEDIATORS IL 1 AND IL 6

The release of IL 1 and IL 6 from monocytes was used as an additional parameter of the degree of inactivation of endotoxins by the compounds tested. Endotoxin was incubated with lactoferrin or with the combination of lactoferrin and immunoglobulin. The supernatant was then incubated together with monocytes and the concentration of the mediators interleukin 1 and interleukin 6 released by the monocytes was measured in the supernatant. Lactoferrin (Lcf.—Fe(A)) with an iron content of 28 μg per gram of lactoferrin as well as lactoferrin (Lcf.—Fe(B)) with an iron content of 296 μg per gram of lactoferrin were used.

The following immunoglobulins were used: 7S IgG enriched with 12% IgM (IgG/A/M=Pentaglobin ®).

Endotoxins from the following bacterial strains were used: Salmonella abortus equi (NOVOPYREXAL®) and the FDA endotoxin standard EC-5 from E. coli 0113:H10:K0.

Lactoferrin, immunoglobulin and lactoferrin combined with immunoglobulin were incubated together with endotoxin at 37° C. for 60 minutes. Human albumin was used as a control. The concentrations of proteins in the preparations were 625 mg/dl, 312 mg/dl and 156 mg/dl respectively. Incubation was carried out with endotoxin concentrations of from 50 to 1500 EU/dl.

Following incubation with the protein, each endotoxin solution was incubated with mononuclear cells from healthy donors (16 hours at 37° C.). Then the concentration of the released mediators IL 1 and IL 6 was determined. IL 1 was measured by means of the fibroblast proliferation test (LOPPNOW, H.; FLAD, H.-D.; ULMER, A.-J. et al. "Detection of Interleukin 1 with Human Dermal Fibroblasts" Immunbiol., 1989, 179, 283–291) using an EL4-6.1 thymoma cell line. The concentration of IL 6 was also determined by means of a proliferation test using an IL 6-dependent murine hybridoma (7TD1) (VAN DAMME J. CAYPHAS S. et al. (1987) Eur. J. Biochem. 168: 543–550; as well as VAN OERS MHJ. VAN der HEYDEN A. and AARDEN LA. (1988) Clin. exp. Immunol. 71: 314–419).

The incubation of endotoxin with lactoferrin resulted in a sharp reduction in the endotoxin-induced release of mediators from the mononuclear cells. This effect is dependent on the iron content of the lactoferrin - it can be improved by raising the iron load. Combining lactoferrin with immunoglobulins further intensifies the suppressant effect on the release of mediators, whereby a higher iron content of lactoferrin also improves the suppressant effect of the combination of lactoferrin with immunoglobulins.

Results:

I. Lactoferrin a) When 500 EU/dl of endotoxin were incubated with Lcf.—Fe(A) the average release of IL 1 was 387 U/ml with *S. abortus* equi and 229 U/ml with *E. coli*. Release of IL 6 was 1,269 U/ml with *S. abortus* equi and 1,971 U/ml with *E. coli*.

b) Following incubation of endotoxin (500 EU/dl) with Lcf.—Fe(B) the average release of IL 1 was 145 U/ml with *S. abortus* equi and 136 U/ml with *E. coli*. The average release of IL 6 was 765 U/ml with *S. abortus* equi and 831 U/ml with *E. coli*.

II. Lactoferrin and IgG/A/M (12% IgM)

Incubation of 500 EU/dl of endotoxin with IgG/A/M (12% IgM) alone average release of IL 1 was 986 U/ml with *S. abortus* equi and 912 U/ml with *E. coli*. Average release of IL 6 was 1,802 U/ml with *S. abortus* equi and 3,387 U/ml with *E. coli*.

B) The addition of lactoferrin to the 7S IgG preparation enriched with 12% IgM (IgG/A/M) led to the following results after incubation with 500 EU/dl of endotoxin at a total immunoglobulin concentration of 312 mg % and a lactoferrin concentration of 312 mg % as well:

a) When the lactoferrin used was Lcf.—Fe(A) the average release of IL 1 was 251 U/ml with *S. abortus* equi and 167 U/ml with *E. coli*. Average release of IL 6 was 920 U/ml with *S. abortus* equi and 1,268 U/ml with *E. coli*.

b) A combination of Lcf.—Fe(B) with IgG/A/M(12%) resulted in an average IL 1 release of 69 U/ml with *S. abortus* equi and 47 U/ml with *E. coli*. Average release of IL 6 under these conditions was 407 U/ml with *S. abortus* equi and 518 U/ml with *E. coli*.

III ALBUMIN

Following incubation of endotoxin (500 EU/dl) with albumin as a reference the average release of IL 1 was 2,975 U/ml with endotoxin from *S. abortus* equi and 2,676 U/ml with *E. coli*. Release of IL 6 was 3,018 U/ml with *S. abortus* equi and 6,233 U/ml with *E. coli*.

C) Influence of lactoferrin on plasma endotoxin activity

Human plasma from healthy donors was diluted 1:10 and inactivated by means of heat [80° C.]. Lactoferrin was then added to obtain a 250 mg/dl plasma lactoferrin concentration. The same amount of albumin was added to the control plasma samples. Endotoxin was then added to the plasma/lactoferrin and plasma/albumin mixtures (Pseudomonas and E. coli endotoxin) to obtain endotoxin activity levels of 1,000 EU/dl and 300 EU/dl in the plasma preparation, which was then incubated for 60 minutes at 37° C. Following this, the endotoxin activity in the sample was measured.

Plasma endotoxin activity was seen to be significantly decreased in the samples by addition of lactoferrin as compared to those containing only albumin.

a) The addition of Lcf.—Fe(A) to the plasma resulted in a reduction in endotoxin activity of $62.1\% \pm 4.8\%$ (n=18) with 1,000 EU/dl endotoxin and $67.4\% \pm 5.4\%$ with 300 EU/dl endotoxin (n=16).

b) The addition of Lcf.—Fe(B) to the plasma resulted in a reduction in endotoxin activity of $78.5\% \pm 6.9\%$ (n=18) with 1,000 EU/dl endotoxin and $84.1\% \pm 5.1\%$ with 300 EU/dl endotoxin (n=20).

Summary evaluation of results:

1. Lactoferrin that has bound trivalent metal ions, such as iron, or bivalent metal ions, such as, for example, zinc, is capable of reducing the biological activity of endotoxin, whereby the level of effectiveness depends on the lactoferrin concentration used.

2. The degree to which lactoferrin reduces the toxic effects of endotoxin increases with the amount of iron bound by the lactoferrin. The iron content of the lactoferrin used should be at least 0.1 $\mu$g per gram of lactoferrin but preferably higher than 100 $\mu$g per gram of lactoferrin.

3. The reduction of the biological activity of endotoxin resulting from the use of lactoferrin in combination with other plasma proteins, in particular immunoglobulins from the IgG and IgM fraction, is significantly greater than when these proteins are used in isolation from one another. The combination of lactoferrin and immunoglobulins has a synergistic effect potentiating the endotoxin-inactivating effects of both proteins.

4. This synergism is characterized by a significant increase in the endotoxin inactivation capacity of the lactoferrin/immunoglobulin combination. In this way, a therapeutically relevant inactivation of endotoxin is achieved without overloading the organism with iron.

5. Although it is also possible to achieve a reduction of endotoxin activity using a combination of iron-free lactoferrin and immunoglobulin, the lactoferrin/immunoglobulin combination with an iron content of at least 0.1 $\mu$g per gram of lactoferrin has proven to be more advantageous. An iron content greater than 100 $\mu$g per gram of lactoferrin is, however, preferable.

6. Because of its ability to reduce the biological activity of endotoxin, lactoferrin is suitable for treatment of toxic effects of endotoxin in cases of reduced endotoxin elimination and in all types of pathological process involving an increased passage of endotoxins out of the intestinal tract, or from a septic focus, into the bloodstream.

7. Since lactoferrin can also be administered directly into the gastrointestinal tract, it is particularly well suited to treatment of endotoxin passage from the intestinal tract into the blood. For this purpose, it can be administered either per os or by means of a tube, as a sole substance or in combination with other substances, in particular such as are used for purposes of enteral nutrition.

8. On account of its greater inactivation capacity, the combination of lactoferrin with immunoglobulins is an adequate therapeutic agent for the treatment of the toxic effects of endotoxins for all pathological processes that result in a passage of larger amounts of endotoxin into the bloodstream from the intestinal tract or a septic focus over longer periods. Lactoferrin or combined lactoferrin/immunoglobulin therapy may therefore be expected to have a favorable effect on the clinical course of endotoxemias, no matter what their cause.

9. Since lactoferrin may lead to inhibition of the release from the macrophages of the colony stimulating factor (CSF) important for granulopoiesis, CSF as required, in either the recombinant or natural form, should be included in i.v. applications of lactoferrin.

10. Lactoferrin that has bound other metal ions instead of iron, such as ions of zinc, copper, cobalt, manganese or magnesium, may also be used to treat the toxic effects of endotoxins.

The various aspects of the invention are further described by the following examples:

EXAMPLE 1

The following experiments were carried out to obtain an objective measure of the significance of the iron load of lactoferrin for inactivation of endotoxin in plasma: Human plasma from healthy donors was diluted 1:10 with 0.9% NaCl, then inactivated by heat (80° C., 5 minutes). Lactoferrin complexed with varying amounts of iron was then added to the plasma. The lactoferrin concentration in these reaction preparations was 300 mg/dl. The iron load of the lactoferrin was adjusted by adding varying amounts of $FeCl_3$ to obtain lactoferrin-to-iron mol ratios of 22:1, 1:1, 1:2.5 and 1:3.9.

After the addition of lactoferrin, endotoxin from Pseudomonas aeruginosa in varying concentrations was also added to the plasma samples, resulting in endotoxin concentrations in the reaction preparation of 50, 100, 200, 300, 500, 750, 1000 and 1500 EU/dl. The preparation was incubated for 60 minutes at 37° C. immediately after the addition of endotoxin. Residual endotoxin activity in the samples was then measured. The inactivation capacity of the various lactoferrin solutions for an endotoxin excess of 10 EU/dl was then calculated on the basis of the values obtained. - Details of the method used to calculate inactivation capacity is described in detail in the section "In vitro tests".

The inactivation capacity values for 100 mg/dl of lactoferrin were calculated as a function of lactoferrin-to-iron mol ratios: The calculations were carried out so as to arrive at an endotoxin excess of 10 EU/dl; the following values resulted:

a) 22:1:17.2 EU per 100 mg of lactoferrin
b) 1:1:68.2 EU per 100 mg of lactoferrin
c) 1:2.5:179.4 EU per 100 mg of lactoferrin
d) 1:3.9:405.7 EU per 100 mg of lactoferrin Inactivation capacity can be increased by raising the proportion of iron of lactoferrin. For example, raising the iron level from a lactoferrin-to-iron mol ratio of 22:1 to 1:3.9 in the lactoferrin preparation increases inactivation capacity by a factor of 23.5. It is expected that at a mol ratio of 1:3.9 the majority of lactoferrin molecules will have bound two molecules of iron each.

EXAMPLE 2

A raised plasma endotoxin activity level was determined in a female patient with a diffuse peritonitis. A 16.5% reduction of endotoxin activity was achieved by incubating a plasma sample from this patient with an immunoglobulin preparation enriched with IgM (for 30 minutes at 37° C.) at an immunoglobulin concentration in the reaction preparation of 312 mg/dl. When the same plasma was incubated with lactoferrin (Lcf.—Fe(A)) in a concentration of 312 mg/dl, 41% of the endotoxins are inactivated. The level of endotoxin inactivation in the patient's plasma was increased to 64% by combining Lcf.—Fe(A) with the immunoglobulin in concentrations of 312 mg/dl in each case.

Adding the same amount of lactoferrin Lcf.—Fe(B) with a higher iron content in corresponding concentration to the patient's plasma inactivated 63% of the endotoxins. Combining this lactoferrin Lcf.—Fe(B) with the IgM-enriched immunoglobulin preparation (IgG-/A/M) resulted in the inactivation of even more endotoxin in the patient's plasma —87%. The effective reduction of endotoxin activity by lactoferrin with iron, and the enhancement of this effect by the combination of lactoferrin containing iron with immunoglobulins, provide a means of treating endotoxemias of any origin using human lactoferrin in intravenous application. Since the release of colony stimulating factor (CSF) may be inhibited by lactoferrin, additional CSF should be substituted as required along with the i.v. lactoferrin application.

EXAMPLE 3 (FIG. 1)

To simulate the conditions occurring in therapy of gram-negative infections with antibiotics, an endotoxin increase in the blood was induced in animal experiments by first inoculating bacteria into the abdominal cavity, then administering a bactericidal antibiotic intravenously, thus causing rapid bacterial decay.

A blood collection catheter was inserted into the right jugular vein of anesthetized Wistar rats (250-300 g). A defined number of three different species of bacteria was then inoculated into the animals' abdominal cavity (E. coli, Klebsiella species and Pseudomonas aeruginosa, each in a concentration of $0.75 \times 10^5$ CFU per kg b.w.). 30 minutes after the bacteria were inoculated into the abdominal cavity the preparation under study (lactoferrin, lactoferrin and immunoglobulin) was administered i.v. through the venous catheter by means of a perfusor in a dosage of 250 mg/kg b.w. The animals in the control group received a corresponding dosage of albumin i.v.. In order to induce an endotoxemia, a bactericidal antibiotic (IMIPENEM=Zienam ®) was administered i.v. one hour after bacterial challenge. Blood samples for purposes of determining the endotoxin activity and the bacterial count in the blood were taken before the bacterial inoculation as well as afterwards at 30-minute intervals over a period of 5 hours. The following preparations were administered i.v.: 7S IgG enriched with 12% IgM (IgG/A/M=Pentaglobin ®); lactoferrin (Lcf.—Fe(A)) with an iron content of 28 μg of $Fe^{3+}$/g, and lactoferrin (Lcf.—Fe(B)) with an iron content of 296 μg of $Fe^{3+}$/g; also lactoferrin (Lcf.—Fe(B)) combined with IgM (12%)-enriched immunoglobulin (IgG/A/M).

Results: (FIG. 1)

a) When albumin was administered, plasma endotoxin activity increased considerably following administration of the antibiotic. An average endotoxin activity of 192 EU/dl was reached as early as one hour after administration of the antibiotic. After four hours, mean plasma endotoxin activity had reached 210 EU/dl.

b) The i.v. administration of IgM(12%)-enriched 7S IgG (IgG/A/M) led to a reduction of plasma endotoxin activity, which, in comparison to the albumin control group, was 46% one hour after administration of the antibiotic and 53% four hours later.

c) When lactoferrin (Lcf.—Fe(A)) was administered i.v. the initial increase in plasma endotoxin activity—one hour after administration of the antibiotic—was reduced by approx. 58.5% in comparison to the albumin control group. Four hours after administration of the antibiotic, endotoxin activity in the animals in the (Lcf.—Fe(A)) group was still 44% lower than in the albumin control group.

d) When lactoferrin (Lcf.—Fe(B)) was administered i.v. the initial increase in endotoxin activity in the plasma—one hour after administration of the antibiotic—was reduced by approx. 75.3% in comparison to the albumin control group. Four hours after administration of the antibiotic the endotoxin activity in the group that had received Lcf.—Fe(B) was still approx. 60.5% lower than in the albumin group.

e) When lactoferrin (Lcf.—Fe(B)) combined with an immunoglobulin enriched with 12% IgM was administered i.v. the initial increase in plasma endotoxin activity—one hour after administration of the antibiotic—was reduced by approx. 73% in comparison to the albumin control group. Four hours after administration of the antibiotic the endotoxin activity in the group that had received this combination was approx. 85% lower than in the albumin control group.

The enhancement of inactivation capacity obtained with the combination of lactoferrin with immunoglobulins makes it possible to control a drastic increase in plasma endotoxin activity even in cases where endotoxin continues to enter the bloodstream over a long period without overloading the body with iron. Application of iron-loaded lactoferrin (Lcf.—Fe(B)) alone effects a reduction similar to that experienced with the lactoferrin/immunoglobulin combination in the initial stage (FIG. 1) when the iron content is lower. Unless either the dosage or the iron load is raised, the inactivation capacity of low-iron lactoferrin alone will in time prove insufficient in cases of continued endotoxin passage into the blood, which may in turn lead to a resurgence of plasma endotoxin activity. The combination of immunoglobulin with lactoferrin represents a very efficient therapeutic alternative, even when lactoferrin with an iron content under 500 µg/g of lactoferrin is used.

EXAMPLE 4 (FIG. 2)

Animal experiments have demonstrated that the transmural passage of macromolecules from the intestine into the blood ma increase 20-fold under immunosuppression with Ciclosporin. Immunosuppression also results in a considerable increase in the passage of endotoxins from the intestine into the blood [Nitsche D, Stehle M, Hamelmann H. Der Einfluß der Immunsuppression mit Ciclosporin auf die enterogene Endotoxinämie: Tierexperimentelle Untersuchungen. Langenbecks Archiv für Chirurgie 1990 (Suppl.)]. This animal model was therefore used to determine the extent to which the passage of endotoxin from the intestinal tract into the bloodstream can be influenced by enteral lactoferrin administration.

Wistar rats were pre-treated with Ciclosporin (12 mg/kg/day; i.m.) for 4 days. Following 12 hours of fasting, a laparotomy was carried out under chloral hydrate anesthesia. A gastric tube was then introduced through the esophagus into the duodenum. Through this tube, the animals then received a suspension of E. coli ($2.5 \times 10^{10}$ CFU/kg of b.w.). Then an antibiotic was administered via the tube (a mixture of 16,250 IU/kg of b.w. of neomycine and 1,250 IU/kg of b.w. of bacitracin). Following administration of the antibiotic, a control group (n=14) received 300 mg/kg of b.w. of 2.5% albumin solution through the tube. The therapy group (n=16) received 300 mg/kg of b.w. of 2.5% lactoferrin solution (bovine lactoferrin) immediately following administration of the antibiotic. The iron content was 845 µg of $Fe^{3+}$/g of lactoferrin.

To determine the plasma endotoxin concentration, 0.2 ml blood samples were taken at sixty-minute intervals from the jugular vein once the duodenal tube was in place over a total period of 5 hours. The blood sample for determination of the zero point was taken prior to laparotomy and bacterial challenge. The endotoxin levels were determined using a modified Limulus test combined with a chromogenic substrate. The fluorescence assay method was used to determine the blood Ciclosporin concentration.

Results

The mean plasma Ciclosporin concentration in the animals was 1,181 ng/ml at the beginning of the experiment. In all of the animals that had been subjected to pre-treatment with Ciclosporin, i.e. the animals in both groups, the zero point values for plasma endotoxin activity were slightly raised at $3.2 \pm 2.7$ EU/dl, which is a direct result of pre-treatment with Ciclosporin. Administration of the antibiotic through the tube resulted in an increase in plasma endotoxin activity in the animals in the albumin control group as well as in those receiving lactoferrin. This effect was registered only 30 minutes later. One hour after administration of the antibiotic there was no significant difference between the plasma endotoxin concentrations in the two groups. As early as two hours after administration of the antibiotic, however, the mean plasma endotoxin concentration in the animals that had received albumin was significantly (p=0.041) higher ($18.7 \pm 3.95$ EU/dl) than in the group that had received lactoferrin through the tube (here the value at this point was $11.27 \pm 5.76$ EU/dl). Whereas the mean plasma endotoxin concentration continued to rise continuously in the albumin group to reach $4.5 \pm 8.52$ EU/dl at the end of the observation period, no significant increase in plasma endotoxin activity was found in the lactoferrin group during the same period. At the end of the observation period, i.e. 5 hours after administration of the antibiotic, the mean plasma endotoxin concentration in the lactoferrin group was $9.48 \pm 3.64$ EU/dl. The difference between this group and the albumin group was highly significant at this point ($p < 0.001$).

The mean plasma endotoxin concentration values in the animals that received lactoferrin through the tube, which remained significantly lower than in the albumin group from the second hour after administration of the antibiotic until the end of the observation period, prove that a therapeutically relevant inactivation of endotoxins in the intestine can be achieved by means of enteral administration of lactoferrin. This attenuation of the enterogenic source of endotoxemia at the same time relieves the load on the plasma's intrinsic mechanism for neutralizing endotoxins. Thus enteral administration of lactoferrin, whether per os or through a tube, is suitable as an adjuvant therapy in treatment of endotoxemia:

a) In septicemia patients, since the enterogenic component of the endotoxemia can be influenced by use of the enteral method of application, which should be carried out in addition to systemic treatment with an endotoxin inactivator.

b) In patients with enterogenic endotoxemias resulting from permeability disturbances in the intestinal tract such as may occur in newborns and are to be expected during immunosuppressive treatment with Ciclosporin.

c) In patients with enterogenic endotoxemias resulting from increased passage of endotoxins from the intestine into the blood such as occurs in inflammatory intestinal condition, e.g. colitis ulcerosa or morbus Crohn and other inflammatory enteritis types.

d) In patients with enterogenic endotoxemias resulting from increased influx of endotoxins from the intestine caused by increased bacterial decay such as may occur under therapy with bactericidal antibiotics.

e) In patients with disturbed hepatic elimination of endotoxins, such as may result from liver maturation disturbance in newborns as well as from all types of parenchymal damage to the liver, obstructive jaundice and decreased RES function.

I claim:

1. A method of protecting animal species from the toxic effects of endotoxins comprising administering to an animal an endotoxin reducing dose of a solution containing lactoferrin bound to a metal ion.

2. A method according to claim 1 wherein the metal ion is selected from the group consisting of iron, zinc, copper, cobalt, manganese and magnesium.

3. A method according to claim 2 wherein the metal ion is iron.

4. A method according to claim 3 wherein the iron content is at least 0.1 ug per gram of lactoferrin.

5. A method according to claim 4 wherein the iron content is at least 100 ug per gram of lactoferrin.

6. A method according to claim 1 wherein the lactoferrin is combined with an immunoglobulin solution.

7. A method according to claim 5 wherein the immunoglobulin solution contains IgG.

8. A method according to claim 6 wherein the immunoglobulin solution contains IgG, IgM and IgA.

9. A method according to claim 3 wherein the solution contains a colony stimulating factor.

10. A method of protecting animal species from the toxic effects of endotoxins comprising administering intravenously to an animal an endotoxin reducing dose of a solution containing lactoferrin bound to a metal ion.

11. A method according to claim 10 wherein the metal ion is selected from the group consisting of iron, zinc, copper, cobalt, manganese and magnesium.

12. A method according to claim 11 wherein the metal ion is iron.

13. A method according to claim 12 wherein the iron content is at least 0.1 per gram of lactoferrin.

14. A method of protecting animal species from the toxic effects of endotoxins comprising administering by a tube to the gut of an animal an endotoxin reducing dose of a solution containing lactoferrin bound to a metal ion.

15. A method according to claim 14 wherein the metal ion is selected from the group consisting of iron, zinc, copper, cobalt, manganese and magnesium.

16. A method according to claim 15 wherein the metal ion is iron.

17. A method according to claim 16 wherein the iron content is at least 0.1 ug per gram of lactoferrin.

* * * * *

REEXAMINATION CERTIFICATE (3424th)

United States Patent [19]

Nitsche

[11] B1 5,240,909

[45] Certificate Issued Jan. 20, 1998

[54] USE OF LACTOFERRIN FOR TREATMENT OF TOXIC EFFECTS OF ENDOTOXINS

[76] Inventor: Dietrich Nitsche, Bismarckallee 2, 2300 Kiel, Germany

Reexamination Request:
No. 90/003,921, Aug. 21, 1995

Reexamination Certificate for:
Patent No.: 5,240,909
Issued: Aug. 31, 1993
Appl. No.: 834,327
Filed: Jan. 13, 1992

[22] PCT Filed: Mar. 13, 1991

[86] PCT No.: PCT/DE91/00214

§ 371 Date: Jan. 13, 1992

§ 102(e) Date: Jan. 13, 1992

[87] PCT Pub. No.: WO91/13629

PCT Pub. Date: Sep. 19, 1991

[30] Foreign Application Priority Data

Mar. 14, 1990 [DE] Germany ................... 4008033

[51] Int. Cl.$^6$ ................... A61K 38/16
[52] U.S. Cl. ................... 514/8; 514/6; 530/395; 530/400; 530/380; 530/387; 530/350; 424/85.1; 424/85.8
[58] Field of Search ................ 514/6, 8; 530/395, 530/400, 380, 387, 350; 424/85.1, 85.8

[56] References Cited

U.S. PATENT DOCUMENTS

| | | | |
|---|---|---|---|
| 4,726,948 | 2/1988 | Prieels et al. | 424/94.4 |
| 4,780,529 | 10/1988 | Hao | 530/350 |
| 5,296,464 | 3/1994 | Tomita et al. | 514/6 |

FOREIGN PATENT DOCUMENTS

| | | |
|---|---|---|
| 63-284133 | 11/1988 | Japan . |
| 3-220130 | 9/1991 | Japan . |

OTHER PUBLICATIONS

Cross et al., Infection & Immunity, pp. 2741–2747, 1993. Review article.

Stedman's Medical Dictionary, pp. 1440, 1447–1448, 1982, 24th Edition.

Dorland's illustrated Medical Dictionary, pp. 1365 and 1746, 27th edition, 1988.

Mustafa et al., J. Infectious Diseases, vol. 160(5) pp. 891–895, 1989.

Cohen et al., The Lancet, pp. 1069–1070, 1985.

Rokke et al., "Bacterial Endotoxins: Pathophysiological Effects, Clinical Significance, and Pharmacological Control," Publishers: Alan R. Liss, Inc., pp. 247–262, 1988.

Broxmeyer et al., J. Clin Invest., vol. 79, pp. 721–730, 1987.

Broxmeyer et al., Immunobiol., vol. 172, pp. 168–174, 1986.

Bezkorovainy, Adv. Exp. Med. Biol., vol. 135, pp. 139–154, 1981.

Ballantyne, The American Surgeon, vol. 50, No. 7, pp. 405–411, 1984.

Ward, J. Burn Care Rehabil., vol. 8, No. 6, pp. 488–491, 1987.

Dorland's Illustrated Medical Dictionary, Twenty–Sixth Edition, W.B. Saunders Co., Philadelphia, 1985.

Harrison's Principles of Internal Medicine, Ninth Ed., McGraw Hill, Inc., New York, 1980.

Cell–Growth Factor Part II: Cellular & Molecular Biology, edited by the Japan Tissue Culture Society, Asakura Shoten, 1987, with attached translation.

Chemical Abstracts, vol. 109, No. 24, Dec. 12, 1988, pp. 325–326.

Imabori et al, "Seikagaku Jiten" 1st Edition, pp. 881 and 1318, Tokyo Kagaku Dojin (1984)(Partial English Translation).

Zagulski et al, British Journal of Experimental Pathology, vol. 70, pp. 697–704 (1989).

Zucali et al, Blood, vol. 74, No. 5, pp. 1531–1536 (1989).

Tracey et al, Nature, vol. 330, No. 17, pp. 662–664 (1987).

Rogers et al, Immunology, vol. 34, pp. 19–28 (1978).

*Primary Examiner*—Chhaya D. Sayala

[57] ABSTRACT

Animal species are treated either intravenously or by tube directly to the gut with a solution containing a lactoferrin bound to a metal ion, the metal ion content being at least 0.1 mg per gram of lactoferrin. The dose is sufficient to inhibit endotoxins.

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–17 are cancelled.

* * * * *